(12) United States Patent
Tadepalli et al.

(10) Patent No.: US 9,216,935 B2
(45) Date of Patent: Dec. 22, 2015

(54) GREEN PROCESS FOR PRODUCING 3-METHYL-3-PENTENE-2-ONE

(71) Applicant: International Flavors & Fragrances Inc., New York, NY (US)

(72) Inventors: Sunitha Rao Tadepalli, Manalapan, NJ (US); Geatesh Karunakaran Tampy, Colts Neck, NJ (US); James Stevens, Atlantic Highlands, NJ (US)

(73) Assignee: International Flavors & Fragrances Inc. NY (US)

( * ) Notice: Subject to any disclaimer, the term of this patent is extended or adjusted under 35 U.S.C. 154(b) by 0 days.

(21) Appl. No.: 14/283,897

(22) Filed: May 21, 2014

(65) Prior Publication Data

US 2015/0133694 A1    May 14, 2015

Related U.S. Application Data

(60) Provisional application No. 61/825,661, filed on May 21, 2013.

(51) Int. Cl.
*C07C 45/72* (2006.01)
*C07C 45/45* (2006.01)
*C07C 45/74* (2006.01)

(52) U.S. Cl.
CPC .............. *C07C 45/45* (2013.01); *C07C 45/74* (2013.01)

(58) Field of Classification Search
CPC ....................................... C07C 45/72
USPC ......................................... 568/390
See application file for complete search history.

(56) References Cited

U.S. PATENT DOCUMENTS

| 4,005,147 | A  | * | 1/1977  | Fischer et al. ............... | 568/390 |
| 4,234,518 | A  | * | 11/1980 | Yoshida et al. .............. | 568/377 |
| 6,603,047 | B2 | * | 8/2003  | Wiese et al. ................. | 568/345 |
| 6,979,751 | B2 | * | 12/2005 | McCusker-Orth et al. ... | 568/345 |
| 7,071,361 | B2 | * | 7/2006  | Barnicki et al. ............. | 568/390 |

FOREIGN PATENT DOCUMENTS

IN    201000331    2/2012

OTHER PUBLICATIONS

Thotla et al. Aldol Condensation of Acetone with Reactive Distillation Using Water as a Selectivity Enhancer. Indian Engineering & Chemical Research, 2007, vol. 46, 8371-8379.*

Database CAPLUS [Online] Chemical Abstracts Service, Columbus US; Feb. 17, 2012, Rao, V., et al., "Method for Continuous Production of 3-methyl-3-penten-2-one", XP002730425, Database accession No. 2012:264725 * abstract* & in 2010 MU 00331 A (Privi Organics Limited, India), Feb. 17, 2012.

Sartori, G., et al., "Dehydration-Hydration of α-Alkynols over Zeolite Catalyst. Selective Synthesis of Conjugated Enzynes and α,β-Unsatuated Ketones", Tetrahedron, vol. 52, No. 24, pp. 8287-8296, (Jun. 10, 1996).

Extended European Search Report for EP14169302.8 issued on Oct. 17, 2014.

* cited by examiner

*Primary Examiner* — Sikarl Witherspoon
(74) *Attorney, Agent, or Firm* — Martin Zhang; XuFan Tseng; Elizabeth M. Quirk

(57) ABSTRACT

The present invention relates to an improved and sustainable process for producing 3-methyl-3-pentene-2-one which is used in the synthesis of fragrance ingredients for perfumery applications.

12 Claims, 2 Drawing Sheets

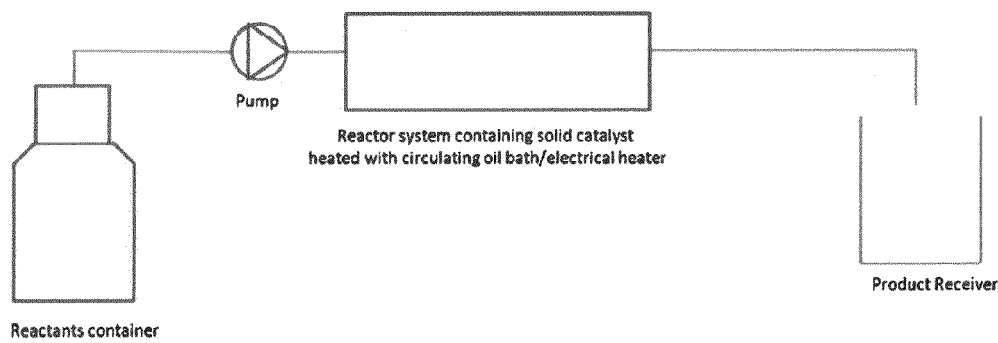
Figure 1. Reactor configuration for the production of 3M3P using premixed reactant(s)/solvent.
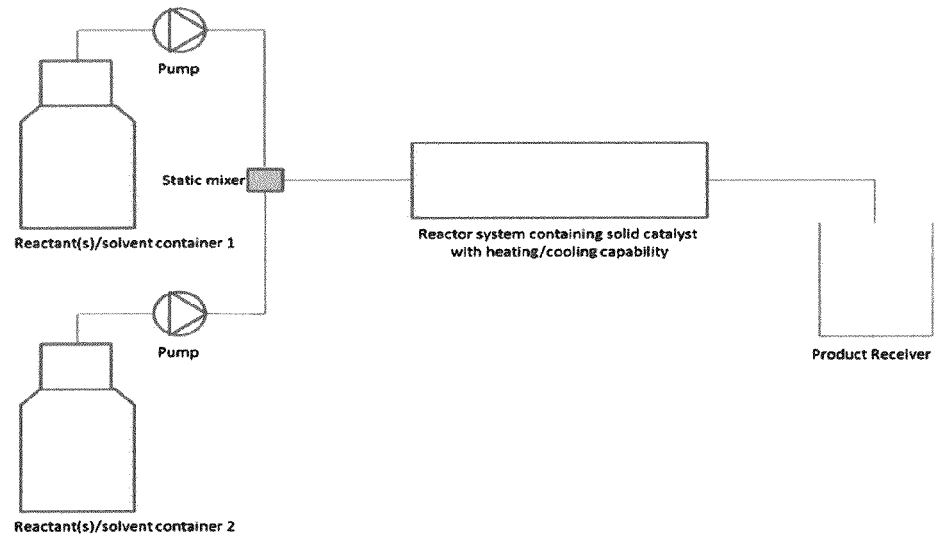
Figure 2. Reactor configuration for the production of 3M3P using in-line mixing of reactant(s)/solvent.

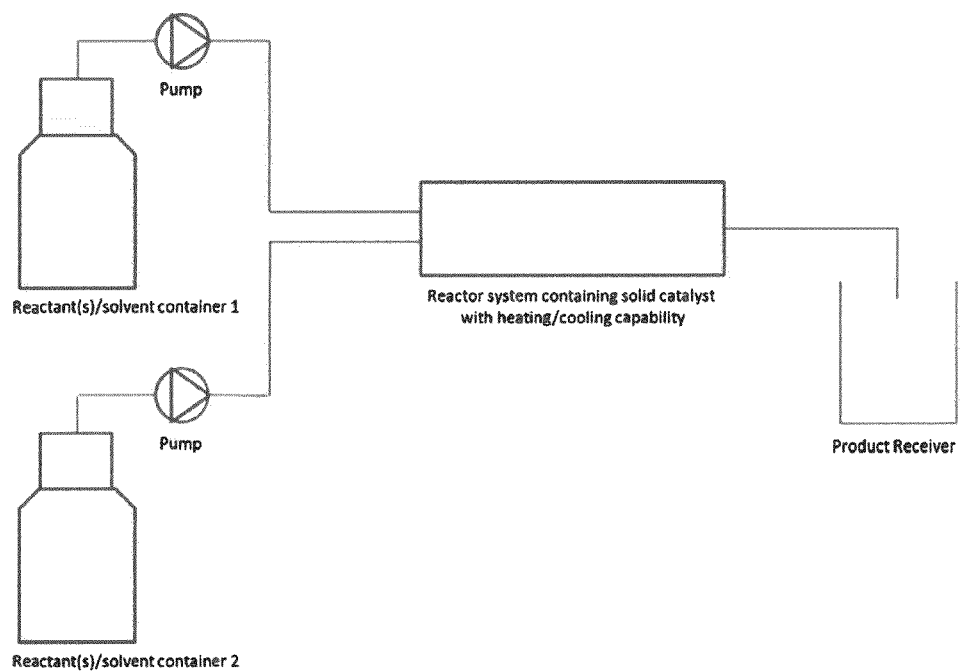
Figure 3. Reactor configuration for the production of 3M3P using multiple feed points.

GREEN PROCESS FOR PRODUCING 3-METHYL-3-PENTENE-2-ONE

STATUS OF RELATED APPLICATIONS

This application claims priority to U.S. provisional patent application Ser. No. 61/825,661, filed May 21, 2013, the contents of which are incorporated herein by reference.

FIELD OF INVENTION

The present invention relates to an improved "greener" process for synthesis of 3-methyl-3-pentene-2-one, a key intermediate in the synthesis of woody fragrance ingredients for perfumery applications.

BACKGROUND OF INVENTION

The synthesis of 3-methyl-3-pentene-2-one (3M3P) involves an aldol condensation reaction between acetaldehyde and methyl ethyl ketone using an acid catalyst. There is limited information available in the literature for this specific reaction. Heiba and Anderson (1959) used carbon tetrachloride for this reaction and reported acetaldehyde conversion of 32% with significant formation of acetaldehyde polymers. U.S. Pat. No. 4,234,518 describes the use of zinc acetate as catalyst for this reaction to give a mixture of 4-hexene-3-one and 3M3P in 31:69 ratio with 38% overall yield.

The industrial process for manufacture of 3M3P generally uses mineral acid catalysts such as sulfuric acid to drive the reaction and is typically conducted in a semi-batch or batch mode in a stirred tank reactor. In such reactor system, the reaction medium needs to be stirred vigorously to overcome the mass transfer limitations between organic reactants and aqueous acid phases to try and maximize the product yield and reduce reaction time. The intensity of mixing is usually a limiting factor in production scale batch reactors, thus resulting in low reactor throughput and product yields. In addition, the process using mineral acids generate huge aqueous waste streams that need to be disposed. Furthermore, due to relatively high water solubility, significant amount of product and reactants are being lost in the aqueous stream, thus further lowering product yield and adding to environmental concerns.

One approach that addresses some of these issues is the use a solid acid catalyst rather than a mineral acid for this chemical transformation. Mahajan et al (2007) studied the use of Amberlyst 15, a solid acid catalyst and developed a kinetic model and Mahajani et al (2009) used this model in a computer simulation exercise to propose a reaction-distillation system for 3M3P. However, the high residence times (60 hours at 70-75° C.) based on simulation results is impractical to be of any value for industrial applications. Typically, higher temperatures are used to increase reaction speed and lower residence time however, in this case higher temperatures (>100° C.) are detrimental to the Amberlyst 15 catalyst, reduces catalyst life and increases cost making the approach uneconomical. Snell et al (2010) have reported the use of solid aluminophosphate catalysts, but the yield of 3M3P they obtained (<6%) was too low to be of practical value.

For practical industrial application of the solid acid catalyst, the combination of a good catalyst with long life, process and operating conditions to achieve high yield of 3M3P in a reasonable reaction time and appropriate reactor design all play a critical role. The present invention discloses a practical 3M3P process using a continuous reactor system and solid acid catalyst with good activity and long life that gives high product yield with low residence time, and essentially no waste.

SUMMARY OF THE INVENTION

The present invention discloses an improved and sustainable process for synthesis of 3-methyl-3-pentene-2-one (3M3P).

According to the present invention, the improved process for 3M3P involves the use of solid acid catalyst for the aldol condensation of acetaldehyde and methyl ethyl ketone in a continuous reactor system.

BRIEF DESCRIPTION OF THE DRAWINGS

FIG. 1: This figure illustrates the setup for the production of 3M3P using premixed reactant(s) and/or solvent.

FIG. 2: This figure illustrates the setup for the production of 3M3P using in-line mixing of reactant(s) and/or solvent FIG. 3: This figure illustrates the setup for the production of 3M3P using multiple feed points of reactant(s) and/or solvent.

DETAILED DESCRIPTION OF THE INVENTION

According to the present invention, the process for the production of 3M3P comprises of reacting a mixture of acetaldehyde and methyl ethyl ketone in the presence of a solid acid catalyst in a continuous reactor system.

According to some embodiments of the present invention, the continuous reactor system may be a single Continuous Stirred Tank Reactor (CSTR) or multiple CSTRs in series.

According to some embodiments of the present invention, the continuous reactor system may be a continuous flow reactor including microreactor.

As used herein, the phrase "reactor" refers to the device where the reaction actually occurs. As used herein, the term "microreactor" and "microchannel reactor" refers to a device or an assemblage of related devices that contains reaction channels in which at least one of the transverse dimensions is sub-millimeter or millimeter range. In some embodiments, the reactor comprised of channels with internal diameter (ID) ranging from 0.2 to 3 mm.

In some embodiments of the present invention, the flow reactor may be a packed bed reactor, wherein the reactor is packed with materials such as catalyst, glass beads (about 10 μm to about 100 μm particle size). As used herein, the terms "packed" and "packing" mean to fill with an amount of material that allow effective production of a pre-determined amount of 3M3P and the amount of material often requires taking into consideration, e.g., the size of the reactor vessel, the material type and the pre-determined amount of 3M3P.

In some embodiments of the present invention, the catalyst for producing 3M3P is a solid acid which may be Natural clay minerals including but not limited to kalonite, bentonite, zeolites and synthetic clays. In some embodiments of the present invention, the catalyst for producing 3M3P is metal oxide and sulfide including but not limited to ZnO, CdO, $Al_2O_3$, $CeO_2$, $TiO_2$, $ZrO_2$, $SnO_2$, PbO, $As_2O_3$, $Bi_2O_3$, $Sb_2O_5$, $V_2O_5$, $Cr_2O_3$, $MoO_3$, $WO_3$, CdS, ZnS. In some embodiments of the present invention, the catalyst for producing 3M3P is metal salt including but not limited to $MgSO_4$, $CaSO_4$, $SrSO_4$, $BaSO_4$, $CuSO_4$, $ZnSO_4$, $Ca(NO3)_2$, $AlCl_3$, $TiCl_3$, $Mg(ClO_4)_2$. In some embodiments of the present invention, the catalyst for producing 3M3P is mixed oxides including but not limited to mixtures of $SiO_2$, $Al_2O_3$, $SnO_2$, $ZrO_2$, MgO, CaO, $Fe_2O_3$, $WO_3$, $Cr_2O_3$, $SnO_2$. In some embodiments of the present invention, the catalyst for producing 3M3P is cation exchange resin or polymeric perflourinated resinsulfonic acid including but not limited to amberlyst, dowex. In some embodiments of the present invention, the solid acid catalyst for producing 3M3P can be made in-house by absorbing a mineral acid or otherwise depositing acidic moities on a solid support.

In some embodiments of the present invention, the process for the production of 3M3P is illustrated by, but not limited to, the following experimental procedure and attached figures. In some embodiments of the present invention, the liquid stream containing the reactants acetaldehyde and methyl ethyl ketone is pre-mixed and is pumped in to the reactor system containing catalyst as shown in FIG. 1. In some embodiments of the present invention, the reactants and/or solvent are mixed in-line using a static mixer before entering the reactor system as shown in FIG. 2. In some embodiments of the present invention, the reactants and/or solvent are fed separately into the reactor system as shown in FIG. 3. In some embodiments of the present invention, the reactor configuration can be a combination of FIGS. 1, 2 and/or 3, thereof. In some embodiments, the reactor system may comprise a catalyst retainer to prevent the catalyst from moving out of the reactor. In some embodiments, the reactor system is heated using a heating circulating oil bath or electrical heater. From the reactor system, the reaction mixture is collected in a product receiver. The reaction mixture is analyzed using Gas Chromatography (GC).

In some embodiments of the present invention, the catalyst volume in the reactor system may vary from 20 to 90%.

In some embodiments of the present invention, the reaction is conducted at temperatures from about 25 to 200° C.

In some embodiments of the present invention, the reaction pressure may vary from 0 psig to 100 psig.

In some embodiments of the resent invention, the liquid stream may comprise of a mixture of two reactants: acetaldehyde, methyl ethyl ketone and/or a solvent. In such embodiments, the concentration of methyl ethyl ketone in the liquid stream may vary from 10 to 90% by weight. In such embodiments, the mole ratio of methyl ethyl ketone to acetaldehyde may vary from 1 to 10.

In some embodiments of the present invention, the liquid stream may comprise of a solvent including, but not limited to, hydrocarbons such as hexane, decane, cylcohexane, decalin; mixture of hydrocarbons such as isopars; alcohols such as methanol, ethanol, iso-propyl alcohol; ketones such as acetone, methyl ethyl ketone; water. In such embodiments, the concentration of solvent in the liquid stream may vary from 0 to 75% by weight.

The following are provided as specific embodiments of the present invention. Other modifications of this invention will be readily apparent to those skilled in the art. Such modifications are understood to be within the scope of this invention. All the reactants and solvents were obtained from Sigma Aldrich. As used herein L is understood to be liter, mL is understood to be milliliter, $m^3$ is understood to be cubic meter, kW is understood to be kilo watts, mol is understood to be moles, psig is understood to be pounds per square inch gauge, g is understood to be gram, kg is understood to be kilogram, min is understood to be minutes and hr to be hour. IFF as used herein is understood to mean International Flavors & Fragrances Inc., New York, N.Y., USA.

Productivity of 3M3P expressed as the yield calculated as, $$Yield = \frac{\text{Moles of product formed}}{\text{Moles of acetaldehyde/Methylethyl ketone consumed in the reactor}}$$

Residence time is calculated as, $$Residence\,time = \frac{\text{Volume of the reactor}}{\text{Volumetric } flowrate \text{ of the reaction mixture}}$$

Mass efficiency is calculated as, $$\text{Mass Efficiency} = \frac{\text{amount of product formed ignoring water}}{\text{total amount of all reagents consumed during reaction}}$$

Below are few examples to describe the state of art disclosed in the present invention. They are not intended to limit the scope of what the inventors regard as their invention nor are they intended to represent that the experiments below are all or the only experiments performed.

EXAMPLES

Synthesis of 3M3P in a Micro Reactor Using Solid Acid Catalyst 2.5 g of solid acid catalyst supported on polymeric resin is packed into a micro reactor of length 20 cm and inner channel diameter 5.3 mm. A mixture of acetaldehyde and methyl ethyl ketone with mole ratio of 1:6 is fed at 0.05 ml/min into the micro reactor which is maintained at 65-70° C. The 3M3P yield (analyzed by GC) is 82 (mol/mol) based on acetaldehyde and 85 (mol/mol) based on methyl ethyl ketone. The residence or reaction time in the micro reactor is ~1 hour. Mass efficiency under these conditions for 40 hours of continuous operation is ~64%.

Synthesis of 3M3P in a Micro Reactor Using Solid Acid Catalyst 2.5 g of solid acid catalyst supported on polymeric resin is packed into a micro reactor of length 20 cm and inner channel diameter 5.3 mm. A mixture of acetaldehyde and methyl ethyl ketone with mole ratio of 1:3 is fed at 0.05 ml/min into the micro reactor which is maintained at 120° C. The 3M3P yield (analyzed by GC) is 75 (mol/mol) based on acetaldehyde and methyl ethyl ketone. The residence or reaction time in the micro reactor is ~1 hour. Mass efficiency under these conditions for 40 hours of continuous operation is ~57%.

Synthesis of 3M3P in a Micro Reactor Using Solid Acid Catalyst 2.5 g of solid acid catalyst supported on clay is packed into a micro reactor of length 20 cm and inner channel diameter 5.3 mm. A mixture of acetaldehyde and methyl ethyl ketone with mole ratio of 1:3 is fed at 0.05 ml/min into the micro reactor which is maintained at 150° C. The 3M3P yield (analyzed by GC) is 50 (mol/mol) based on acetaldehyde and methyl ethyl ketone. The residence or reaction time in the micro reactor is 30 minutes. Mass efficiency under these conditions for 40 hours of continuous operation is ~38%.

Synthesis of 3M3P in a Single CSTR Using Solid Acid Catalyst 1.1 kg of solid acid catalyst supported on polymeric resin charged into CSTR containing methyl ethyl ketone. The reaction mass is heated to 65-70° C. and is run under autogenous pressure. A mixture of acetaldehyde to methyl ethyl ketone mole ratio of 1:6 is fed into the reactor and product mix is continuously removed from the reactor. The 3M3P yield (analyzed by GC) is 82 (mol/mol) based on acetaldehyde and 85 (mol/mol) based on methyl ethyl ketone. The residence or reaction time in the CSTR is ~6 hours. Mass efficiency under these conditions for 600 hours of continuous operation is ~41%.

Comparative Example of 3M3P in the Semi-Batch Reactor Using Conventional Liquid Catalyst Sulfuric acid and methyl ethyl ketone at 1:4 ratio is charged into a semi-batch reactor. The reactor is heated to 65-70° C. and is run under autogenous pressure. Acetaldehyde is fed into the reactor over 4 hours. Then the reaction mass is aged until reaction completion. The 3m3p yield (analyzed by GC) is 65 (mol/mol) based on acetaldehyde and 74 (mol/mol) based on methyl ethyl ketone. The total time for the process is ~10 hours. Mass efficiency under these conditions is ~26%.

What is claimed is:

1. A process for the production of 3-methyl-3-pentene-2-one (3M3P), the process comprising reacting acetaldehyde and methyl ethyl ketone in the presence of a solid acid catalyst in a continuous reactor system, wherein the solid acid catalyst is a solid acid catalyst supported on a polymeric resin, an acid supported on clay, a polymeric perfluorinated resin sulfonic acid, or a combination thereof.

2. The process of claim 1, wherein the continuous reactor system is a single CSTR or multiple CSTR in series.

3. The process of claim 1, wherein the continuous reactor system is a microreactor.

4. The process of claim 3, wherein the continuous reactor system is a packed bed reactor comprising of a packing material selected from the group consisting of a glass bead, a solid acid catalyst and a mixture thereof.

5. The process of claim 4, wherein the solid acid catalyst is a solid acid catalyst supported on a polymeric resin.

6. The process of claim 1, wherein the mole ratio of methyl ethyl ketone to acetaldehyde is from about 1 to about 10.

7. The process of claim 1, wherein the process is carried out using a solvent.

8. The process of claim 1, wherein the catalyst has a volume in the reactor system ranging from 20 to 90%.

9. The process of claim 1, wherein the process has a temperature from about 25 to about 200° C.

10. The process of claim 1, wherein the process is carried out under a pressure from about 0 to about 200 psig.

11. The process of claim 1, wherein the continuous reactor system contains channels each having an internal diameter ranging from 0.2 to 5.3 mm.

12. The process of claim 1, wherein 3M3P is obtained at a mass efficiency of 41% or greater.

* * * * *